United States Patent
Bloch-Salisbury et al.

(10) Patent No.: US 10,251,552 B2
(45) Date of Patent: Apr. 9, 2019

(54) METHODS AND SYSTEMS FOR REDUCING IRRITABILITY IN INFANTS

(71) Applicant: University of Massachusetts Medical School, Worcester, MA (US)

(72) Inventors: Elisabeth Bloch-Salisbury, Worcester, MA (US); David Paydarfar, Newton, MA (US)

(73) Assignee: University of Massachusetts Medical School, Worcester, MA (US)

( * ) Notice: Subject to any disclaimer, the term of this patent is extended or adjusted under 35 U.S.C. 154(b) by 51 days.

(21) Appl. No.: 15/127,744

(22) PCT Filed: Mar. 3, 2015

(86) PCT No.: PCT/US2015/021999
§ 371 (c)(1),
(2) Date: Sep. 20, 2016

(87) PCT Pub. No.: WO2015/143430
PCT Pub. Date: Sep. 24, 2015

(65) Prior Publication Data
US 2017/0172411 A1 Jun. 22, 2017

Related U.S. Application Data

(60) Provisional application No. 61/968,972, filed on Mar. 21, 2014.

(51) Int. Cl.
*A61B 5/00* (2006.01)
*A61B 5/0205* (2006.01)
(Continued)

(52) U.S. Cl.
CPC ............... *A61B 5/00* (2013.01); *A61B 5/024* (2013.01); *A61B 5/02055* (2013.01); *A61B 5/08* (2013.01);
(Continued)

(58) Field of Classification Search
CPC ....... A61B 5/00; A61B 5/02055; A61B 5/024; A61B 5/08; A61B 5/11; A61B 5/4824; A61B 5/6892; A61H 2201/0146
(Continued)

(56) References Cited

U.S. PATENT DOCUMENTS

| | | | |
|---|---|---|---|
| 2008/0242957 A1 | 10/2008 | Gaspard | |
| 2015/0045608 A1* | 2/2015 | Karp | A47D 15/008 600/28 |

FOREIGN PATENT DOCUMENTS

| | | | |
|---|---|---|---|
| WO | WO 2013/033433 A2 | 3/2013 | |
| WO | WO 2013033433 A2 * | 3/2013 | ........... A61B 5/6892 |
| WO | WO 2013/059625 A1 | 4/2013 | |

OTHER PUBLICATIONS

E. Bloch-Salisbury et al, "Stabilizing Immature Breathing Patterns of Preterm Infants Using Stochastic Mechanosensory Stimulation", Journal of Applied Physiology, vol. 107, No. 4, Oct. 1, 2009 (pp. 1017-1027) (11 pages).
(Continued)

*Primary Examiner* — Michael J Carey
(74) *Attorney, Agent, or Firm* — Nixon Peabody LLP

(57) ABSTRACT

Systems and methods according to the present concepts reduce irritability in infants, such as infants suffering from neonatal abstinence syndrome (NAS) or colic. According to one embodiment, a method for reducing irritability in an infant includes determining one or more physiological measurements from an infant. The one or more physiological measurements relate to a state of irritability in the infant. The method also includes determining the state of irritability based on the one or more physiological measurements and applying a stochastic stimulation to the infant based on the state of irritability. The stochastic stimulation may be applied via a mattress. The stochastic stimulation may be vibro-tactile or subsensory.

8 Claims, 8 Drawing Sheets

(51) Int. Cl.
*A61B 5/024* (2006.01)
*A61H 23/02* (2006.01)
*A61B 5/08* (2006.01)
*A61B 5/11* (2006.01)

(52) U.S. Cl.
CPC .............. *A61B 5/11* (2013.01); *A61B 5/4824* (2013.01); *A61B 5/4836* (2013.01); *A61B 5/6892* (2013.01); *A61H 23/02* (2013.01); *A61H 23/0236* (2013.01); *A61B 2503/04* (2013.01); *A61H 2201/0146* (2013.01); *A61H 2201/0188* (2013.01); *A61H 2201/5048* (2013.01); *A61H 2201/5058* (2013.01); *A61H 2201/5061* (2013.01); *A61H 2201/5092* (2013.01)

(58) Field of Classification Search
USPC .................................................. 600/300, 301
See application file for complete search history.

(56) References Cited

OTHER PUBLICATIONS

International Search Report, PCT/US2015/021999, dated Jun. 22, 2015 (5 pages).
Written Opinion of the International Searching Authority, PCT/US2015/021999, dated Jun. 22, 2015 (9 pages).

\* cited by examiner

METHODS AND SYSTEMS FOR REDUCING IRRITABILITY IN INFANTS

CROSS-REFERENCE TO RELATED APPLICATIONS

This application is a U.S. National Stage of International Application No. PCT/US2015/021999, filed Mar. 23, 2015, titled "Methods And Systems For Reducing Irritability In Infants," which claims priority to and the benefit of U.S. Provisional Patent Application No. 61/968,972, filed Mar. 21, 2014, titled "Methods And Systems For Reducing Irritability In Infants," each of which is hereby incorporated by reference herein in its entirety.

GOVERNMENT SUPPORT

This invention was made with government support under grant no. DA035355 awarded by the National Institutes of Health. The government has certain rights in the invention.

FIELD OF THE INVENTION

The present invention relates generally to systems and methods for reducing irritability in infants, and more particularly, to systems and methods that reduce irritability in infants suffering from neonatal abstinence syndrome (NAS) or colic.

BACKGROUND

Neonatal Abstinence Syndrome (NAS)

Irritability in infants may be caused by Neonatal Abstinence Syndrome (NAS). Fetal drug exposure is a nationwide problem. The U.S. Department of Health and Human Services reported that in 2009-2010 nearly 4.5 percent of pregnant women exposed their unborn child to illicit drugs in utero, with greatest prevalence among teen pregnancies (15-17 years, 16.2%) and young adult pregnancies (18-25 years, 7.4%; compared to 26-44 years, 1.9%). Recent estimates of fetal exposure to licit drugs and prescription medications are also remarkable (10.8% alcohol; 16.3% tobacco), with a nearly five-fold increase in ante partum maternal opiate use between 2000 and 2009. NAS refers to drug withdrawal symptoms and multi-system disturbances that occur following termination of drug/s to which an infant has developed physical tolerance and dependence (e.g., observed at birth when fetal and maternal circulations are separated). Over 3% of every 1000 hospital births nationwide have been diagnosed with NAS (i.e., approximately one infant per hour) and upwards of 90% of drug-exposed newborns present with NAS. Hospitalization costs associated with treatment of NAS infants, excluding subsequent neurobehavioral and psychosocial care, are estimated at nearly $750 million annually in the United States.

NAS has been associated with sleep deprivation, disorganization and fragmentation. Fetal exposure to drugs commonly results in central, autonomic, vasomotor and gastrointestinal instabilities in the neonate. Respiratory complications have been identified as the most prevalent disturbance of withdrawal, e.g., increased apnea (i.e., long pauses in breathing that can result in blood-oxygen desaturation), irregular or periodic breathing and tachypnea. This is not surprising since the newborn respiratory oscillator is inherently vulnerable to respiratory dysrhythmias, and maternal smoking and other fetal drug exposure further compromise the developing respiratory control system by impairing central chemosensitivity and altering neurotransmitter systems and neural circuits.

Notably, drug withdrawing infants are at high risk for sudden infant death syndrome due to depressed ventilatory drive and abnormal respiratory patterning. Infant withdrawal symptoms also include persistent irritability marked by excessive movement, crying and sleep disruption, instability of heart rate (bradycardia and tachycardia), and problems with thermoregulation (sweating) and feeding (vomiting and diarrhea).

Approximately 7-9% of the 600 bed annual occupancy in the NICU/CCN at UMass Memorial comprises NAS newborn infants who require morphine for opiate withdrawal (non-iatrogenic). In 2010-2011, the average length of stay was six weeks at a cost of ~$1100/day (i.e., nearly $2 million/year in NAS hospitalization costs). Tools that can alleviate drug withdrawal, reduce hospitalization, and improve outcomes in NAS are warranted.

While research has focused on factors that may affect symptoms and dysregulated neurobehaviors of NAS (e.g., drugs of exposure, epigenetic changes, genetic risks, socioeconomic influences), precise pathophysiology has yet to be described and optimal intervention strategies remain inadequate. Novel approaches to the study and treatment of NAS are needed to facilitate weaning and minimize hospitalization compounded by prolonged pharmacological management, with implications for improved developmental outcomes and reduced medical costs for this at-risk population.

Colic

Irritability in infants may also be caused by colic. Infants who are diagnosed with colic do not suffer from a medical problem but generally experience episodes of crying that last more than three hours, on more than three days a week, for more than three weeks. Colic typically occurs in infants between two weeks and four months of age. It is estimated that up to twenty-five percent of infants may experience colic.

The cause of colic is generally unknown. Crying episodes resulting from colic usually begin at the same time of the day, often in the evening. The symptoms of colic often begin suddenly. Associated symptoms may include legs pulled up to the stomach, a flushed face, clenched hands, and a wrinkled brow. The cry is often high pitched and piercing.

Colic has been previously associated with intestinal causes. Colic, for example, may be triggered by foods or medicines passed through breast milk or by sensitivity to proteins in formula. Infants who have colic are very difficult to comfort and soothe.

SUMMARY

Systems and methods according to the present concepts reduce irritability in infants, such as infants suffering from neonatal abstinence syndrome (NAS) or colic. According to one embodiment, a method for reducing irritability in an infant includes determining one or more physiological measurements from an infant. The one or more physiological measurements relate to a state of irritability in the infant. The method also includes determining the state of irritability based on the one or more physiological measurements and applying a stochastic stimulation to the infant based on the state of irritability. The stochastic stimulation, for example, can be applied via a mattress or portable pad. Alternatively, the stochastic stimulation can be applied, for example, by a device built into an infant carrier, a car seat, or clothing worn by the infant. The stochastic stimulation may be vibro-tactile or subsensory.

In some cases, the infant suffers from Neonatal Abstinence Syndrome (NAS) and the one or more physiological measurements indicate symptoms of NAS relating to the state of irritability. The one or more physiological measurements may relate to at least one of respiration, heart rate, temperature, or movement. Applying stochastic stimulation may reduce physiological instabilities in at least one of the respiration, the heart rate, or the temperature, and the reduction in the physiological instabilities reduces subsequent movement and irritability.

In other cases, the infant suffers from colic and the one or more physiological measurements indicate symptoms of colic relating to the state of irritability. The one or more physiological measurements may relate to at least one of respiration, heart rate, temperature, movement, or crying. The one or more physiological measurements may indicate crying lasting for more than three hours, and the stochastic stimulation is applied in response to crying that lasts for more than three hours.

In according with one embodiment, a system is directed to reducing irritability in an infant. The system includes a sensor for monitoring a physiological instability of an infant, the sensor outputting a measurement signal corresponding to the physiological instability. The system further includes a controller communicatively coupled to the sensor for receiving the measurement signal, the controller determining and outputting a stimulation signal for treating the physiological instability based on the measurement signal. The system further includes an active region having an actuator and being communicatively coupled to the controller, the actuator applying, in response to the stimulation signal, a stochastic stimulation to the infant.

In accordance with another embodiment, a method is directed to reducing irritability in an infant and includes determining, via one or more sensors, one or more physiological measurements from an infant, the one or more measurements relating to a state of irritability in the infant. The method further includes determining, via a controller communicatively coupled to the one or more sensors, the state of irritability based on the one or more physiological measurements, and applying, via an actuator, a stochastic stimulation to the infant based on the state of irritability.

In according with yet another embodiment, an isolation mattress is directed to reducing irritability in an infant. The mattress includes a sensor for measuring an infant physiological condition that is related to one or more of Neonatal Abstinence Syndrome (NAS) and colic. The mattress further includes an active region for interacting with parts of an infant body that require stochastic stimulation, the active region having at least one actuator for applying, based on the measured infant physiological condition, the stochastic stimulation to the parts of the infant body. The mattress also includes a passive region for interaction with parts of an infant body that are sensitive to stochastic stimulation, the passive region being positioned near and mechanically isolated from the active region such that the stochastic stimulation is only applied within the active region. The mattress further includes one or more vibration inhibitor elements for dampening vibrations caused by actuator.

Additional aspects of the invention will be apparent to those of ordinary skill in the art in view of the detailed description of various embodiments, which is made with reference to the drawings, a brief description of which is provided below.

Figure 1:
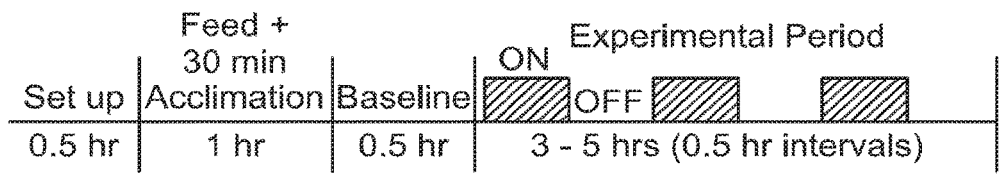
FIG. 1 illustrates a schematic of an example protocol for a study relating to the application of stochastic, vibro-tactile stimulation to NAS infants via a mattress, according to the present concepts.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DESCRIPTION

Neonatal Abstinence Syndrome (NAS)

Embodiments employ the therapeutic benefits of stochastic, vibratory stimulation to enhance timely alleviation of NAS withdrawal. Such stimulation can facilitate physiological stability and serve as a complementary intervention for NAS and reduce weaning courses with morphine, associated hospitalization, and lead to improved outcomes in NAS infants.

Where stochastic resonance is applied in nonlinear systems for therapeutic management of dysrhythmias, it has been shown that: (1) neural activity can be enhanced by stimulus inputs having specified intensities and spectral properties; (2) vibratory mechanical stimuli with specific intensities, frequencies and somatosensory locations enhance transduction of cutaneous mechanoreceptors in animals, sensory perception in humans, and proprioception and balance in elderly and patients with neurological disorders; and (3) stochastic, vibro-tactile stimulation improved respiratory stability and blood-oxygenation in preterm infants. Data support the hypothesis that receptors beneath the vibratory surface (cutaneous, musculoskeletal and visceral mechanoreceptors) project to brain centers to improve function and that stochastic resonance may provide an optimal perturbation for stabilizing dysregulated behaviors.

As part of care management, NAS infants are commonly isolated and environmental stimuli (sound, light, touch) are minimized because of hypersensitivity to stimuli that often exacerbates irritability. This is despite well-established evidence among humans and animals of the importance of environmental enrichment especially during critical periods of early brain development for establishing and refining anatomical, molecular and functional growth. Recent studies have suggested that artificial tactile stimulation can compensate for inadequate maternal care (i.e., separation) by promoting physiological maturation and brain development, and that both prenatal and postnatal tactile stimulation reorganize brain structures and behaviors implicated in fetal drug exposure. Advantageously, applying vibro-tactile stimulation to NAS infants may enhance normal development of neural circuitry. NAS irritability may spread from subcortical, brainstem structures to more rostral cortical areas, such that cardio-respiratory instabilities precede excessive periods of movement. Reducing pathophysiological instabilities in respiration, heart beat and temperature via stochastic, vibro-tactile stimulation ultimately may also reduce subsequent upsurge of movement and the progressive spread of NAS irritability from subcortical to cortical structures.

Figure 8A:
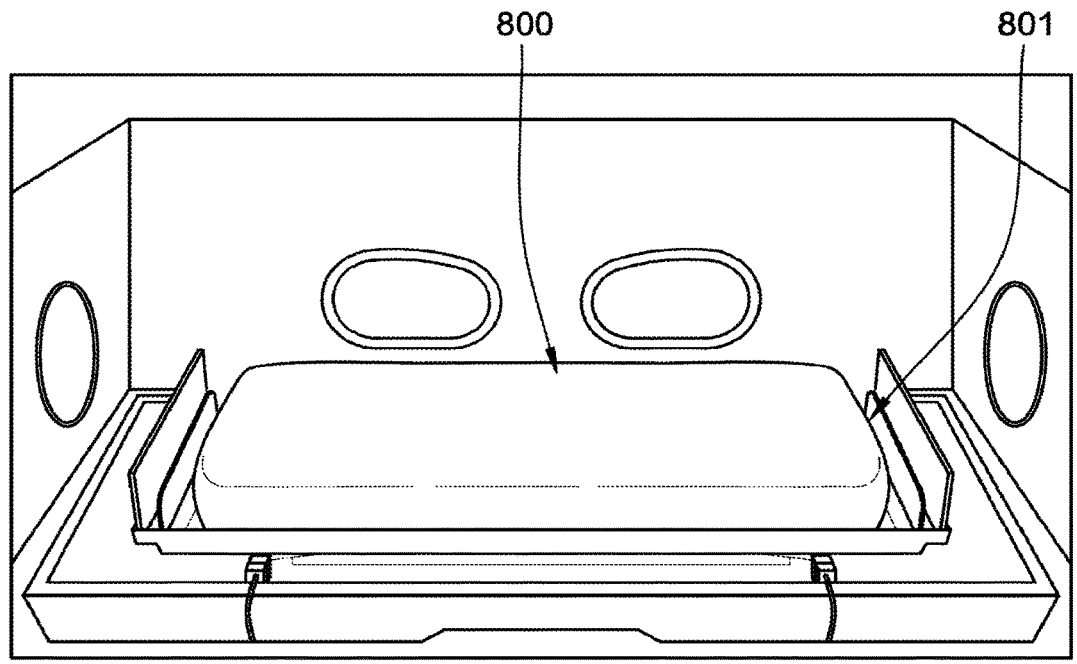
FIG. 8A illustrates a mattress in a hospital bed setting for applying stochastic, vibro-tactile stimulation to infants, according to the present concepts.
Figure 8B:
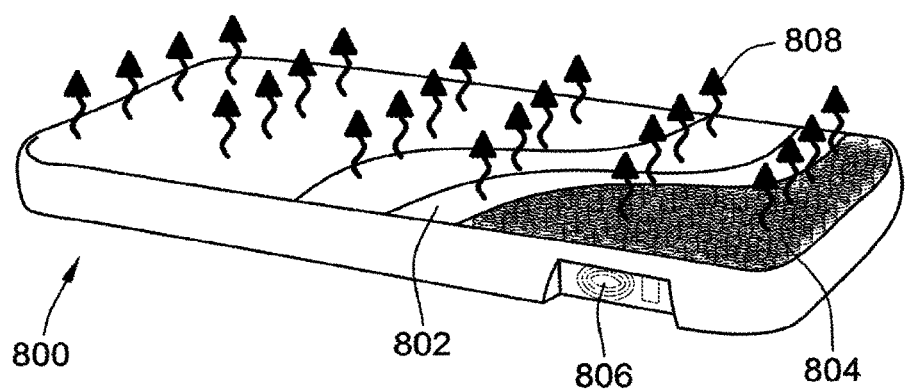
FIG. 8B illustrates a perspective view of specific components of the mattress of FIG. 8A.

As shown in FIGS. 8A and 8B, particular embodiments may employ a mattress 800 (TheraSound, Inc; Wyss Institute, Harvard University) configured to provide a stochastic, vibro-tactile stimulation that enhances physiological stability and alleviates symptoms of drug withdrawal in NAS infants. The mattress includes mechanical actuators 804 and is driven, for example, by a low voltage electric current to provide 30 to 60 Hz of stochastic vibration with a RMS amplitude range of approximately 0.010 to approximately 0.025 mm. It is understood, however, that the stimulation characteristics are not limited to these values and can be adjusted (e.g., increase in amplitude) to increase therapeutic effect. Another example mattress for providing stochastic, vibro-tactile stimulation is described in further detail below in reference to FIG. 9. Although the present concepts may be described herein with reference to a specially configured mattress, it is understood that vibro-tactile stimulation appropriate for the treatment may be applied with other similarly configured devices, e.g., chairs, baby blankets, portable pads, car seats, baby carriers, clothing, etc.

Studies have been performed to determine feasibility and logistics of applying and maintaining sensors in withdrawing, irritable infants and to determine practical durations for using the specially designed mattress in accordance with infants' NICU schedules. A schematic of an example protocol for such a study is illustrated in FIG. 1. Each study begins upon arousal prior to feeding (or medication), at which time sensors are applied to the infant and signals are displayed and recorded. Following a 30 minute post-feed acclimation period, there is a 30 minute baseline period. This data generates baseline information on cardio-respiratory intervals, temperature and state-related activities (movement periods) prior to any stimulus intervention, not confounded by potential habituation or persistent effects of mattress intervention. After baseline, there is on average three to five hours to administer scheduled 30 min intervals of mattress stimulation (ON) alternated with 30 min intervals of no stimulation (OFF); the order of condition intervals are counterbalanced among subjects. In a subset of infants, subsequent experimental periods may be performed to allow for assessment of responses over the course of a day/night cycle. The vibro-tactile stimulation may (1) improve cardio-respiratory control, e.g., reduces bradycardia, tachycardia, apnea, periodic breathing and tachypnea; (2) decrease irritability and sleep disruption indexed by gross body movements; and (3) reduce other NAS symptoms (e.g., instability of temperature, bouts of crying, hiccups).

The study design allows systematic quantification of the effects of vibro-tactile stimulation on breathing (IBI variance), cardiac rhythm (R-R variance), gross body movements (durations >5 seconds; defined via streamlined video, artifact in pulse-oximeter plethysmographic activity), blood oxygenation (durations <85%; variance), and skin temperature (variance). Stimulation may impinge on neural oscillators that drive breathing and cardiac control. Parametric tests are used for analyses of all continuous variables. The Friedman's and Wilcoxon signed-rank tests are used for nonparametric analyses. For analyses of parametric data, separate repeated measures ANOVAs test effects of stimulus condition (ON or OFF) and trial order. Post-hoc pairwise t-tests determine differences in responses for conditions of stimulation ON and OFF. Time of intervention (e.g., infant age, severity of NAS) is a covariate to assess whether there are critical periods in infant development for optimizing stochastic, mechanical stimulation as a therapeutic strategy. Pearson product moment correlation coefficient analysis is used to establish associations between breathing stability (IBI variance) and movement duration, where greater variance in respiratory parameters may be positively correlated with excessive movement. Time series of movement periods and temperature changes are analyzed using Wavelet derived scale average power (SAP) throughout the baseline and intervention periods of ON and OFF stimulation to evaluate temporal dynamics including: (1) response time for improvement in rhythm relative to the onset of stimulation; (2) whether there is loss of efficacy over time (during each 30 min stimulus period as well as from one period to the next); (3) whether improvement in rhythm persists following offset of stimulation; if so, the time course is estimated. P values of <0.05 are considered significant.

The studies allow comprehensive estimates of physiological instabilities in withdrawing infants, and allow infants to serve as their own control during paired ON-OFF stimulation cycles for full characterization of temporal changes among several physiological indices. This allows also for analyses of relationships among cardio-respiratory control and movement.

Figure 2:
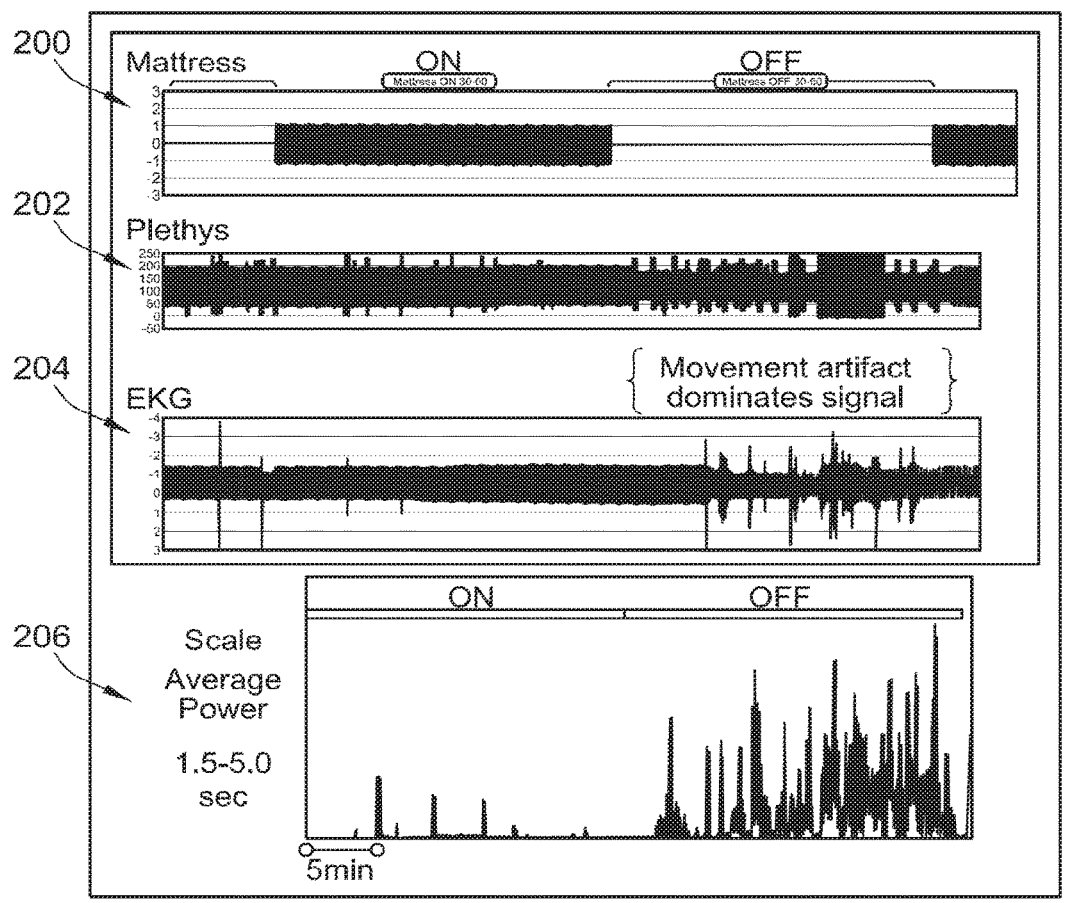
FIG. 2 illustrates an example of reduced movement during the application of stochastic, vibro-tactile stimulation to a NAS infant via a mattress, according to the present concepts.

FIG. 2 illustrates reduction in movement with mattress stimulation 200 in one infant, indexed by a decrease in signal artifact in the pulse-oximeter plethysmograph (Plethys) 202 and in EKG 204 during Mattress ON. FIG. 2 further illustrates the immediate and nearly constant increase in artifact due to movement in these signals during Mattress OFF. The bottom panel 206 of FIG. 2 shows the Wavelet analysis, which quantifies timing (onset/offset and duration) and strength of movement periods from the Plethys signal 202 (Scale Average Power).

Figure 3:
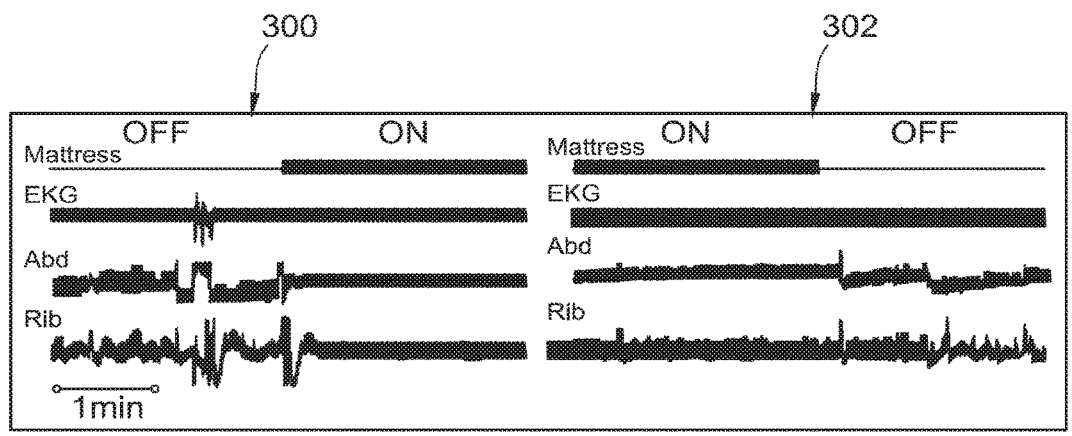
FIG. 3 illustrates an example of improved stability of eupneic breathing during the application of stochastic, vibro-tactile stimulation to a NAS infant via a mattress, according to the present concepts.

FIG. 3 shows two snapshots 300, 302 representative of improved stability in eupneic breathing (Abdominal and Rib, respiratory inductance plethysmography) with Mattress ON in the same infant using a different time scale. Preliminary analysis in eight infants revealed a trend in reduction in variance of interbreath intervals (IBI) (p=0.059) with stimulation, supporting the importance for broader, multi-channel evaluation that encompasses cardio-respiratory control, thermoregulation, and movement activity. Based on background and preliminary studies, vibro-tactile stimulation corroborates an improvement in cardio-respiratory stability and marked reduction in excessive movement in NAS infants.

Figure 4:
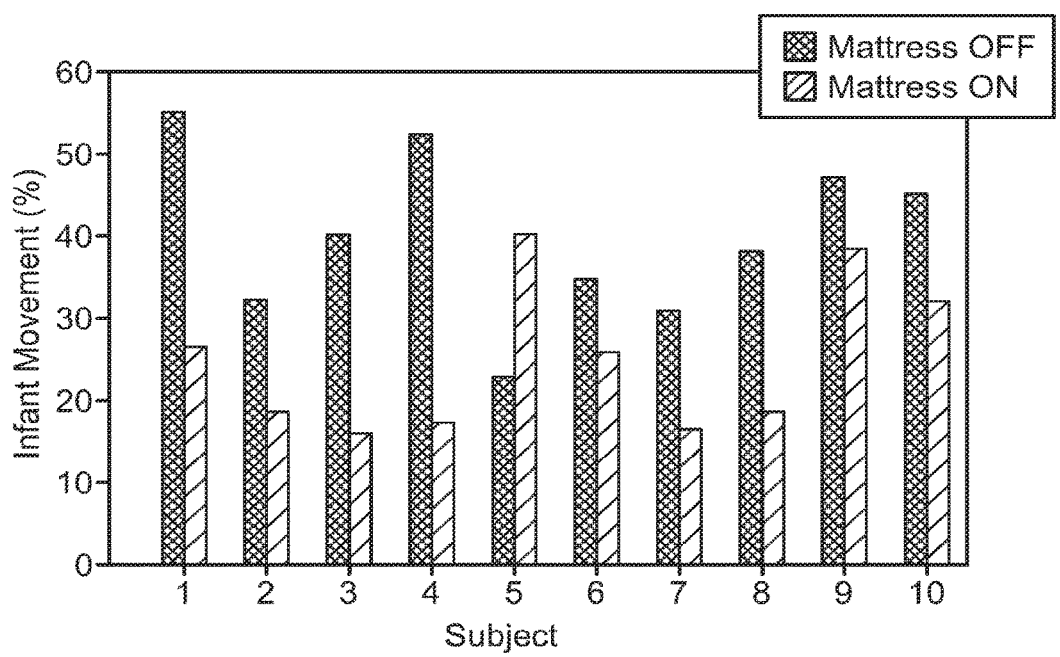
FIG. 4 illustrates example data on infant movement during ON and OFF the application of stochastic, vibro-tactile stimulation to NAS infants via a mattress, according to the present concepts.
Figure 5:
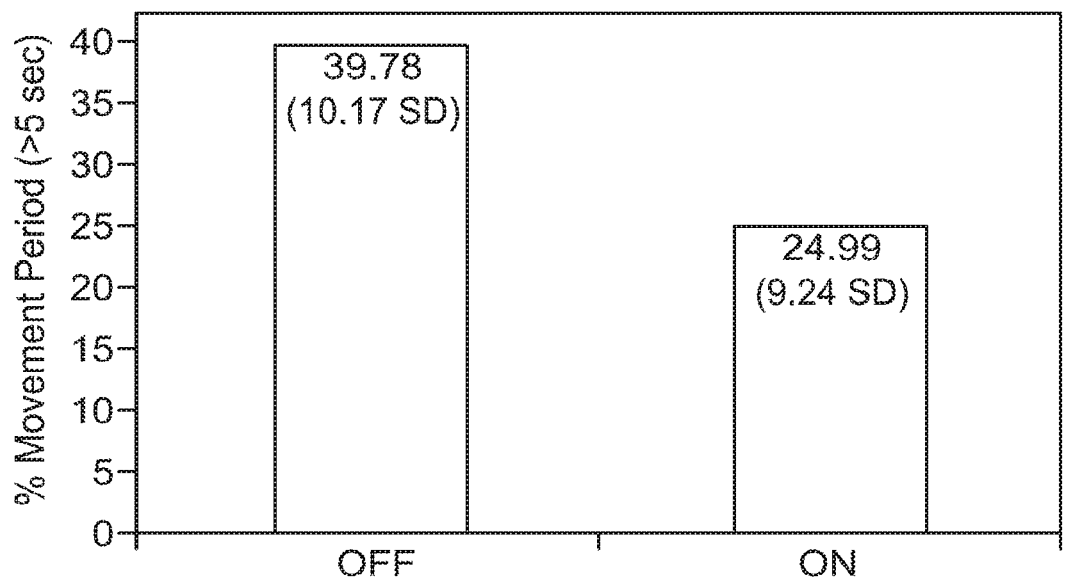
FIG. 5 illustrates the reduction of infant movement during the application of stochastic, vibro-tactile stimulation to NAS infants via a mattress, corresponding to the data of FIG. 4.

FIG. 4 illustrates a chart representative of infant movement during Mattress OFF versus Mattress ON (n=10). The movement period is defined by >5 second distortion of the transcutaneous pulse-oximeter plethysmographic signal (wavelet). The chart is normalized for valid condition time (i.e., excludes nursing interventions). The mean condition duration is 29.77 minutes, with SD=0.58. Correspondingly, FIG. 5 illustrates a significant reduction in infant movement during Mattress ON (in which stimulation is applied) versus Mattress OFF (in which no stimulation is applied). Stimulation produces a 37% decrease in movement. The results reflect a reduction in sleep disruption and fragmentation.

A greater understanding of physiological changes associated with NAS, and a complementary intervention for enhancing cardio-respiratory control and sleep may reduce neurobehavioral and developmental consequences of drug-withdrawal. Currently there is no consensus on an optimal clinical, objective NAS scoring system nor is there a consistent standardized evidence-based treatment protocol for NAS. NAS infants typically require prolonged hospitalization for pharmacological management of withdrawal based on clinical assessments of withdrawal symptoms. Pharmacological interventions, while well established, often comprise weaning courses that vary among and within institutions due in part to different types of opioid agonists for management and also due to a variety of available scoring tools, inconsistency among interpretation of assessment scales, and thresholds for treatment.

Embodiments correlate physiological signals with currently used clinical assessments for NAS. In particular, embodiments use advanced computational models for examining commonly monitored physiological signals, for example, in the NICU setting. Onsets/offsets of dysregulated neurobehaviors may be indicated, and specific instabilities in physiological signals may correlate with particular assessment measures that can provide an objective marker of NAS severity. Embodiments provide a powerful tool for objectively identifying NAS severity and enables improved, individualized pharmacological management of withdrawal in neonates.

Embodiments quantify, via intensive measurement, the instabilities of physiological signals at different stages of drug withdrawal in NAS infants. NAS infants are vulnerable to a host of physiological instabilities that necessitate prolonged hospitalization for pharmacological management. Using nonlinear computational models, quantifiable changes and relationships among physiological signals in NAS infants may provide an objective index for NAS severity to facilitate management of drug withdrawal. In particular, there may be specific changes in movement period, breathing, heart rate and temperature, as well as relationships among these signals that provide objective severity indices and mark physiological predictors of the withdrawal process. The multitude and half-life of drugs of exposure may be included as covariates that influence onset, duration and severity of neurobehavioral instabilities.

To quantify the instabilities of physiological signals at different stages of drug withdrawal in NAS, various techniques may be employed to collect measurements and recordings. For example, respiratory inductance plethysmography may be used to measure infant's breathing (Somonstar). Respitrace bands (SensorMedics) may be placed around the infant's chest wall and abdomen to record respiratory muscle movements, and allow for detection of interbreath intervals (IBI) of respiration. Electrodes over the skin surface of the chest may be used to record electrocardiographic activity (ECG), and allow for detection of R-R intervals of the ECG signal (index of interbeat heart rate). A probe attached to the infant's foot or wrist may measure arterial-blood oxygen concentration (Masimo). Quality of the plethysmographic activity characterized in the pulse signal may allow for identification of movement periods. Movement periods will be assessed further via actigraphy and overt behavioral data may be recorded using a camera with a wide-angled lens placed in the infant's crib. Infant skin temperature may be measured continuously with a sensor placed under the infant's armpit or back (Physitemp). A sound and light meter placed near the infant's head may record sound frequency and intensity, and changes in light level (Extech). Medical history (including toxicology screen on infant) and demographic data may be obtained from infant and mother.

Physiological data may be digitally recorded (~50-1 kHz samples per channel) using an acquisition system that directly obtains signals from the NICU bedside monitor (Philips; Wyss Institute, Harvard University) or via an independent system (Embla). These acquisition systems enable fully synchronized recordings of physiological signals, audiometry, photometry and digital video images. Comments regarding routine nursing assessments and other relevant information (e.g. feeding, pharmacological dosing) may be typed and time stamped along with the physiological data stream. All signals and video images and germane data (e.g., medical histories of infant and mother, NAS severity assessments) may be archived using an open source format in accordance with IRB and HIPPA regulations.

Objective physiological measures among respiration, heart rate, temperature and/or movement may indicate NAS severity. In particular, cardio-respiratory and temperature instabilities and excessive movement may be associated with high severity assessments. It is possible to determine those physiological instabilities that best indicate NAS severity that warrant pharmacological management, and ultimately determine trends in physiology that predict CNS dysregulation.

Signal processing algorithms, using a point processing modeling framework, may characterize separately the instability of respiration and heartbeat. These algorithms track in real time the dynamic and stochastic characteristics of the physiological signal; the stochastic characteristics of respiratory inter-breath intervals (MI) and cardiac beat-to-beat intervals (RR) are integrated with the dynamic characteristics. For example, the IBI time series (a set of discrete points) may be computed and an interpolation of IBI may be derived that provides an instantaneous estimate of mean, variance and other higher order moments along with dynamic measures such as spectrum, poles and frequency. These measures indicate temporal dynamics of the respiratory and heart rate rhythm, as well as corresponding physiological relationships. For example, IBI changes that reflect caudal brainstem function may precede cortical behaviors such as arousal (e.g., movement). In conjunction with this point-process modeling framework, an algorithm using the point process model of RR may be applied with the original respiration signal as a covariate to determine dynamic fluctuations of cardio-respiratory coupling during the withdrawal process.

Because movement and temperature do not have physiological measures that can be considered as a point process, a wavelet-based algorithm may be used to determine the instability of these signals. Wavelet analysis is a powerful tool for examining different rhythms at multiple time scales. It allows analysis of frequency content of a signal as a function of time in order to capture instability based on various spectral distributions while maintaining multi-time scale properties of the signal. An average spectrum (scale average power; SAP) is obtained from the spectrum of frequency ranges. SAP of movement may have unique relationships with the withdrawal process, such as with specific NAS severity measures on clinical assessments. Putative 'triggers' (e.g., instability of respiratory and cardiac rhythms) may be modeled as covariates of movement and it is possible to calculate the probability that changes in cardio-respiratory instabilities (e.g., RR and IBI variability, respectively) are followed by excessive movement periods. Reliable long term multi-channel recordings provide the starting point for developing such models.

Figure 6:
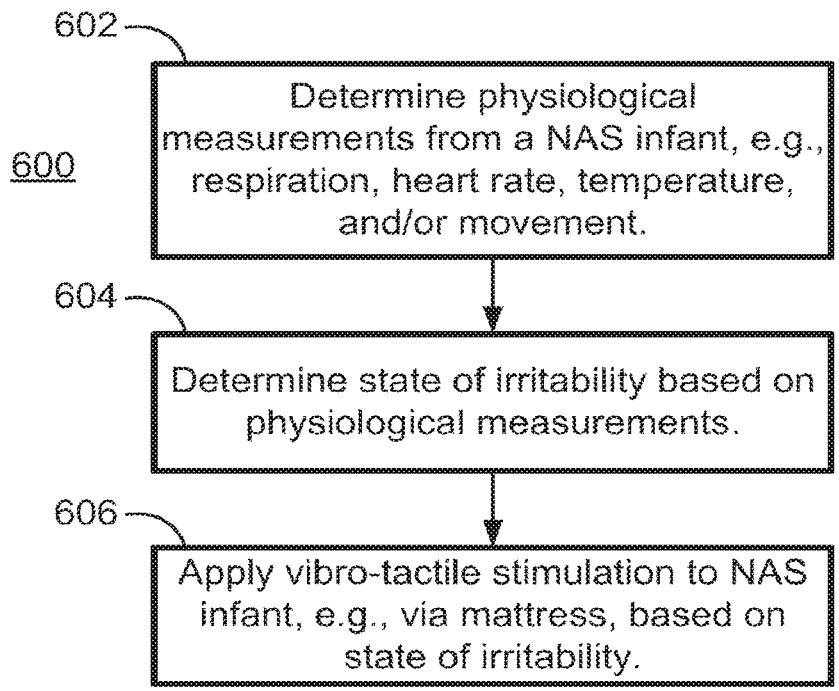
FIG. 6 illustrates an approach for treating NAS infants, according to the present concepts.

Referring to FIG. 6, an approach 600 for treating NAS infants is illustrated. Step 602 takes measurements of respiration, heart rate, temperature, and/or movement, e.g., with sensors, to monitor physiological instabilities in real time. Step 604 receives the physiological measurements and determines a corresponding state of irritability for the NAS infant. In response to the determination of the state of irritability, step 606 applies a corresponding vibro-tactile stimulation to treat the NAS infant. As described above, the infant may be placed in contact with a device (e.g., a mattress) configured to deliver the vibro-tactile stimulation. The vibro-tactile stimulation provided by the mattress may (1) improve cardio-respiratory control, e.g., reduces bradycardia, tachycardia, apnea, periodic breathing and tachypnea; (2) decrease irritability and sleep disruption indexed by gross body movements; and (3) reduce other NAS symptoms (e.g., instability of temperature, bouts of crying, hiccups). The system may continue to take measurements to provide real-time feedback so that the vibro-tactile stimulation may be adjusted according to changes in the physiological measurements. In some embodiments, a controller, e.g., a computer processor, may be employed to process the physiological measurements and control the level of vibro-tactile stimulation. The vibro-tactile stimulation can be turned on and turned off for a predefined period of time. Alternatively, the vibro-tactile stimulation can remain continuously on until a change in one or more of the physiological measurements are detected. Further, the nature of the vibro-tactile stimulation can change over time such that the amplitude, frequency characteristics, and/or period of vibration can change over time.

Accordingly, commonly monitored physiological signals, e.g., in the NICU, may objectively identify NAS severity and vibro-tactile stimulation may provide an adjuvant treatment of NAS. The vibro-tactile stimulation may provide intervention for facilitating drug withdrawal by reducing pathophysiological instabilities. For example, intervals of vibro-tactile stimulation may reduce cardio-respiratory instabilities and irritability marked by excessive movement.

Colic

Infants with colic tend to be unusually sensitive to stimulation. In particular, such infants become easily overwhelmed by lights, sounds, and other stimulation. As described above, NAS infants are commonly isolated and environmental stimuli (sound, light, touch) are minimized because of similar hypersensitivity to stimuli that often exacerbates irritability. This suggests that the vibro-tactile stimulation that reduces irritability in NAS infants may also be effective in reducing irritability in infants with colic. Therefore, the present concepts are not limited to the treatment of NAS infants.

Figure 7:
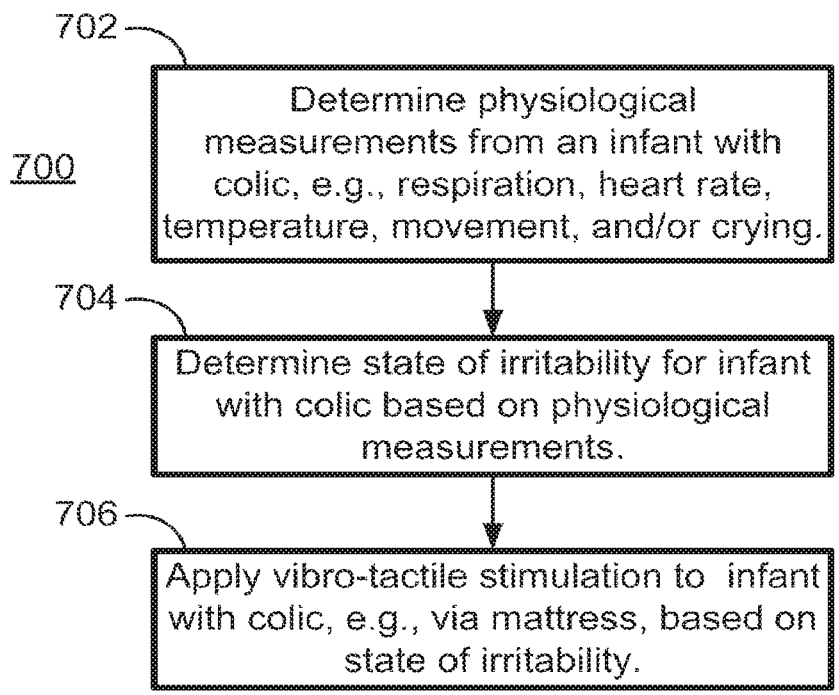
FIG. 7 illustrates an approach for treating infants with colic, according to the present concepts.

Referring to FIG. 7, an approach 700 for treating infants with colic is illustrated. Step 702 takes measurements, e.g., with sensors, to monitor physiological instabilities in real time. Step 702 may measure respiration, heart rate, temperature, and/or movement. Additionally or alternatively, step 702 may measure aspects of the infant's crying, e.g., length, volume, etc., as an indicator for colic. Step 704 receives the physiological measurements and determines a state of irritability for the infant with colic. In response to the determination of the state of the infant, step 706 applies a corresponding vibro-tactile stimulation to treat the infant. As described above, the infant may be placed in contact with a device (e.g., the infant may be placed on a mattress) specially configured to deliver the vibro-tactile stimulation. The vibro-tactile stimulation provided by the mattress may decrease irritability and sleep disruption indexed by gross body movements and/or crying. The system may continue to take measurements to provide real-time feedback so that the vibro-tactile stimulation may be adjusted according to changes in the physiological measurements. In some embodiments, a controller, e.g., a computer processor, may be employed to process the physiological measurements and control the level of vibro-tactile stimulation. The vibro-tactile stimulation can be turned on and turned off for a predefined period of time. Alternatively, the vibro-tactile stimulation can remain continuously on until a change in one or more of the physiological measurements are detected. Further, the nature of the vibro-tactile stimulation can change over time such that the amplitude, frequency characteristics, and/or period of vibration can change over time.

Although the embodiments illustrated in FIGS. 6 and 7 may take measurements to monitor physiological instabilities in real time and determine a state of irritability for the infant, e.g., to provide real-time feedback, other embodiments may provide a more open-loop configuration and may apply a corresponding vibro-tactile stimulation to treat the infant without making such measurements.

Mattress

Referring to FIGS. 8A and 8B, a mattress 800 is supported by a frame structure 801 and includes a mattress foam material 802, a plurality of mechanical actuators 804, and a low voltage input device 806. The mechanical actuators 804 apply a vibro-tactile stimulation 808 to the top surface of the mattress 800. Thus, according to this example, the mattress 800 applies the vibro-tactile stimulation 808 for treating irritability in infants caused by NAS or colic conditions.

Figure 9:
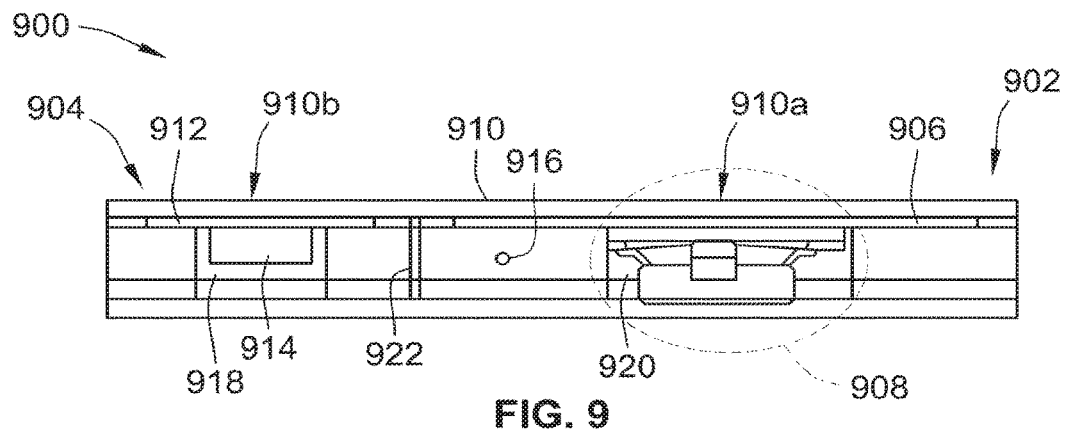
FIG. 9 illustrates an example isolation mattress for applying isolated stochastic, vibro-tactile stimulation to a portion of the isolation mattress, according to the present concepts.

While the mattress shown in FIGS. 8A and 8B may provide vibro-tactile stimulation across most of the mattress area, FIG. 9 depicts an isolation mattress 900 that applies isolated stochastic resonance vibro-tactile to a specific portion of the mattress according to one embodiment. The isolation mattress 900 may be employed to deliver the stimulation, for example, to a NAS infant or an infant with colic as described above. The isolation mattress 900 includes a body 916. The body 916 includes an active region 902, a passive region 904, a top surface 910a, 910b, and a plurality of voids 918, 920, 922. The active region 902 includes an actuator 908 attached to an active soundboard 906. The passive region 904 includes an inertial device 914 attached to a passive soundboard 912. A passive-section void 918 is located around the inertial device 914. An active-section void 920 is located around the actuator 908. A soundboard void 922 is located between the active and passive soundboards 906, 912.

The active region 902 interacts with parts of an infant's body that can receive stimulation with little or no adverse consequences. These body parts include, for example, the legs and torso of the infant. The active region 902 is generally rectangular and occupies top surface 910a area, which is about two-thirds of the isolation mattress 900. It is contemplated that other shapes and sizes may be used be used to obtain the above described benefits.

The active soundboard 906 and the actuator 908 impart vibrational stimulation on the top surface 910a in the active region 902. The actuator 908 is attached to the active soundboard 906 such that movement of the actuator 908 moves the active soundboard 906. The active soundboard 906 is disposed below the top surface 910a such that at least a portion of the vibrations are imparted on the top surface 910a. For example, the active soundboard 906 can be placed approximately one-half inch below the top surface 910a. It is contemplated that other distances may be employed to achieve desired physical and vibrational properties of the top surface 910. For example, the soundboard may be placed from 0.4 inches to 0.6 inches, from 0.25 inches to 0.75 inches, from 0.1 inches to 1.0 inch, or even greater than 1.0 inch from the top surface 910.

The passive region 904 interacts with parts of an infant's body that are more sensitive to stimulation, such as the head. The passive region 904 is shown as being generally rectangular and occupies top surface 910a area, which is about one-third of the total top surface area of the isolation mattress 900. It is contemplated that other shapes and sizes may be used be used to obtain the above described benefits. It is additionally contemplated that the size of the active region 902 relative to the passive region 904 may be altered.

The passive region 904 is mechanically isolated from the active region 902. The inertial device 914 is attached to the passive soundboard 912 such that the inertial device 914 helps to dampen vibrations from the active soundboard 906 and actuator 908. In the illustrated embodiment, the inertial device 914 is a passive inertial device a mass attached to the passive soundboard 912. This mass is 660 g of aluminum rigidly attached to the passive soundboard 912. It is contemplated that the masses may be made of different materials or weights. It is also contemplated that the inertial device 914 may be a device that actively cancels vibrations imparted on the passive soundboard 912.

The body 916 may comprise various materials. By way of non-limiting example, an open-cell foam, gel, or other viscoelastic material may be used to damp the vibrations from the active soundboard 906 and the actuator 908. Additionally, the voids 918, 920, 922 assist in inhibiting vibrations from passing to the passive section. The passive-section void 918 prevents or inhibits vibrations from being imparted to the inertial device 914. The active-section void 920 prevents or inhibits the actuator 908 from imparting vibrations on the body 916. The soundboard void 922 prevents or inhibits vibrations from directly passing between the active soundboard 906 and the passive soundboard 912. It is also contemplated that any or all of the plurality of voids may be replaced with visco-elastic damping materials that alter and/or modify the transmission of vibrations from the active soundboard 906 and actuator 908 to the passive region 904. By way of non-limiting example, Young's Modulus, density, and/or visco-elastic properties may be considered when selecting materials. Sufficiently dissimilar material may result in improved isolation characteristics because vibration transmission between materials is a function of the area of contact in addition to the impedance of the materials to a specific type of vibration.

Additionally, the isolation mattress 900 may indicate the active and the passive regions 902, 904 to an individual. Examples of this include using visual indicia on the top surface 910, the body 916, and/or on a cover placed over the isolation mattress 900. The cover may be made from, for example, polymeric materials including medical grade vinyl.

Figure 10:
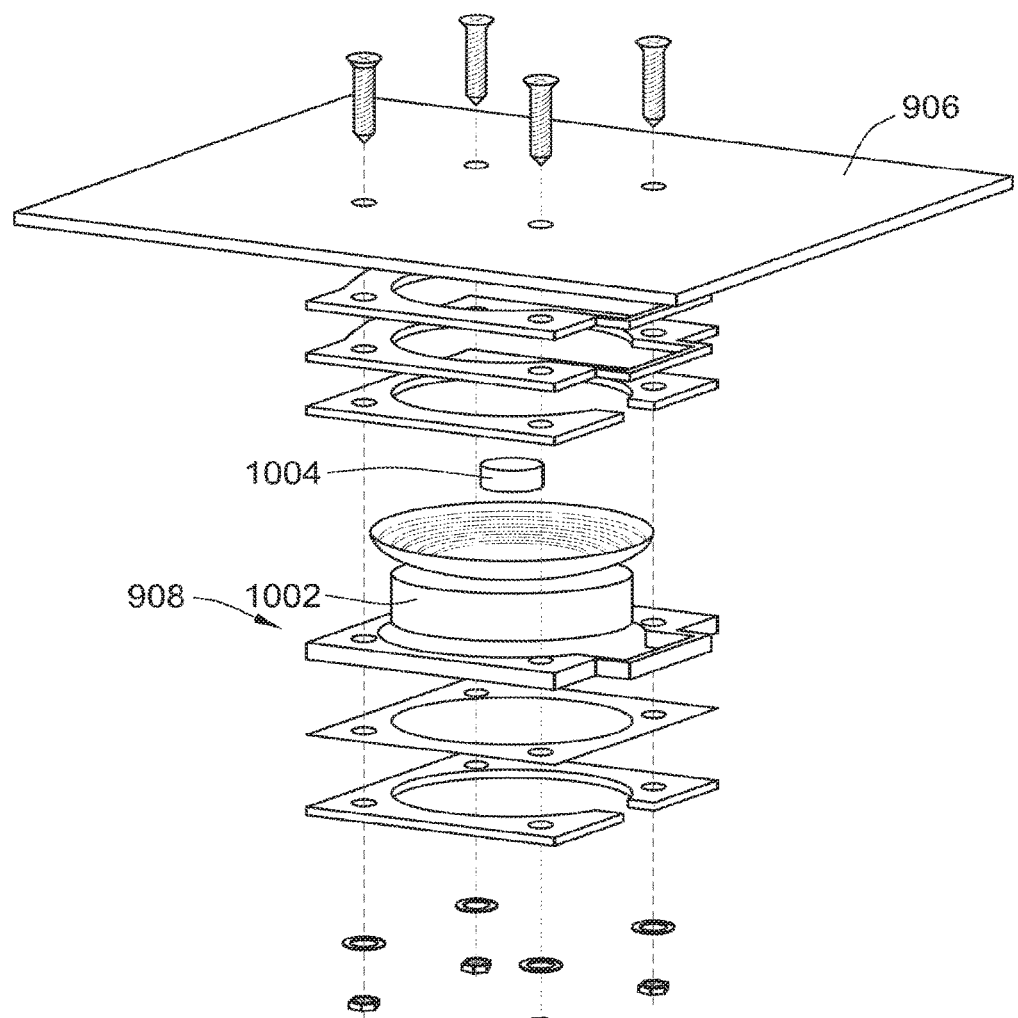
FIG. 10 illustrates an active assembly for the isolation mattress of FIG. 9, according to the present concepts.

Referring now to FIG. 10, an exploded view of the actuator 908 is shown with the active soundboard 906 according to one embodiment. In the illustrated embodiment, the movement of the actuator 908 is obtained by imparting a drive signal to an audio driver 1002. A mass 1004 was added to the audio driver 1002 to increase output.

The isolation mattress 900 was tested against a single-bodied mattress. Both mattresses were 23 inches long, 12 inches wide, and 3.25 inches tall. All soundboards were located one-half inch below the top surface of the mattress.

The specifications for the single-bodied mattress included: an active soundboard being plywood; an actuator being a "woofer" audio driver of unknown origin; a body being a low-density foam rubber material; and the surface covering being a vinyl material.

The specifications for the isolation mattress 900 used in testing included the following specifications: the active and passive soundboards 906, 912 were acrylic plastic; the inertial device 914 was a 660 gram aluminum mass; the actuator 908 was an MCM model 1170 "woofer" audio driver that was modified to remove the driver cone and shorten the overall height; a 38.6 gram mass made of 304 stainless steel was added to the audio driver; and the body was low-density polyurethane foam rubber material (UL94HF-1).

The first signal source consisted of a waveform generator connected to Class A/B current amplifier. This source was used to drive 2V peak-to-peak sinusoidal voltages in order to determine the transfer function of the isolation mattress 900 in the frequency band of interest. The frequencies used were: 10 Hz, 20 Hz, 30 Hz, 40 Hz, 50 Hz, 60 Hz, 70 Hz, 80 Hz, 90 Hz, 100 Hz and 200 Hz. These individual frequencies were used to de-convolve the system transfer function, but the results are not described herein. The second input source was a signal generator configured in the 30 Hz to 60 Hz range at various output settings (e.g. turns). Due to limited availability of the Balance Engineering generator for part of the testing, the third signal source consisted of ten 100 second recordings of the loaded output of the Balance Engineering generator from 1 turn to 10 turns (in 1 turn increments), sampled at 10 kSps, played back via National Instruments LABVIEW SignalExpress software and a National Instruments PCI-6281 Data Acquisition card connected a custom Class A/B current amplifier.

Figure 13:
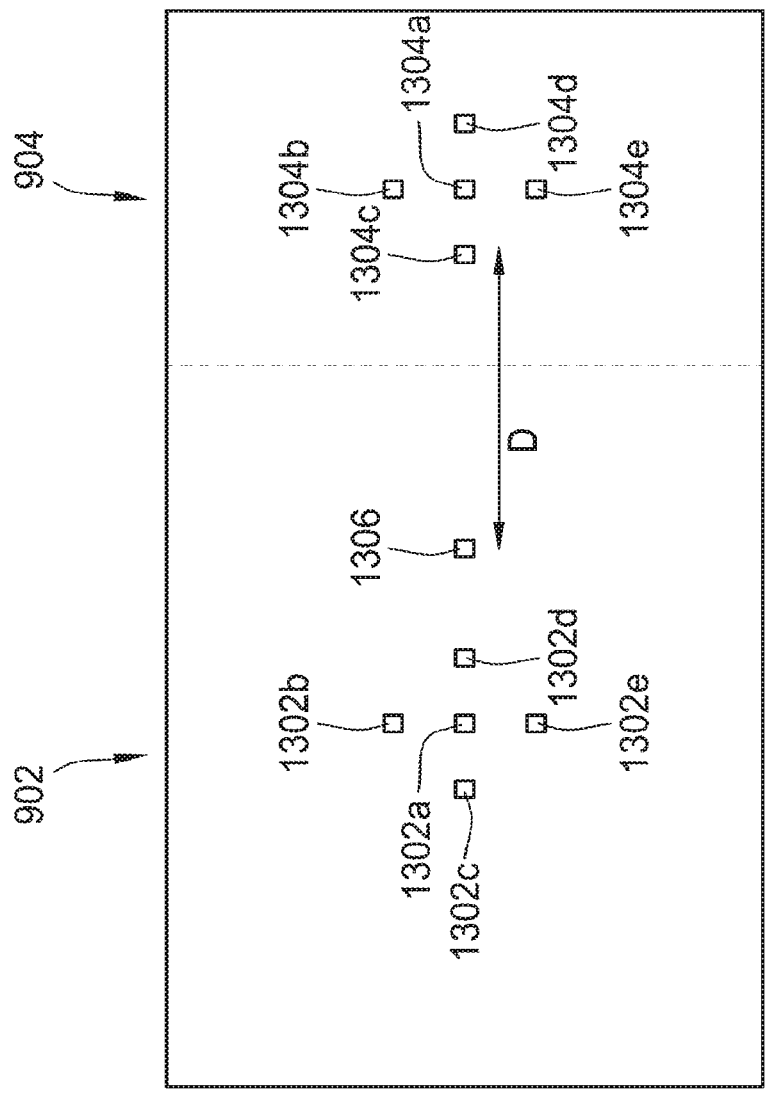
FIG. 13 illustrates a diagrammatic of the isolation mattress of FIG. 9 marked with reflective tape for accurate displacement measurements.

The isolation mattress was marked with reflective tape for accurate displacement measurements with the MTI-2100. As seen in FIG. 13, tape was placed at centers 1302a, 1304a of the active and passive regions 902, 904, respectively. Tape was also placed at points three inches above, to each side of, and below the centers 1302a, 1302b (1302b-e and 1304b-e, respectively) for a total of ten measurement locations. Measurements were also taken to determine the delivered stimulus and percentage isolation for the head if the infant were placed on the physical center point 1306 of the isolation mattress 900 rather than being placed on the center 1302a of the active region 902. Point 1304c was used to describe displacement at the infant's head because it was 5" away from the mattress center 1306. As with the previous characterization, surface displacement measurements were collected using the MTI-2100 Fotonic Displacement system on an air table.

All measurements with the MTI-2100 system were taken using a Model 2062R fiber optic probe in its Range 1 measurement configuration. The linear range for the Model 2062R probe the Range 1 configuration was 152 μm with a nominal sensitivity of 0.025 μm. Each recording period was 100 seconds for every test, regardless of stimulus type. The output of the MTI-2100 system was recorded at 10 kSps and stored into a text file using a Tektronix MSO4034B digital oscilloscope. The stimulus drive voltage and drive current were also recorded at this frequency.

The recorded results were processed using MATLAB® in a similar manner to the methods of the previous characterization. Symmetric 3-pole high-pass Butterworth filters (cut-off of 1 Hz) and low-pass Butterworth filters (cut-off of 4 kHz) were applied to the data. The power spectral density was calculated using Welch's method with a spectral frame size of 1 Hz and a resolution sensitivity of 1.1 Hz. The Root-Mean-Squared value for output displacement was computed using a single window because it yielded more accurate results with less computational time than a sliding window of 0.1 seconds.

Figure 11:
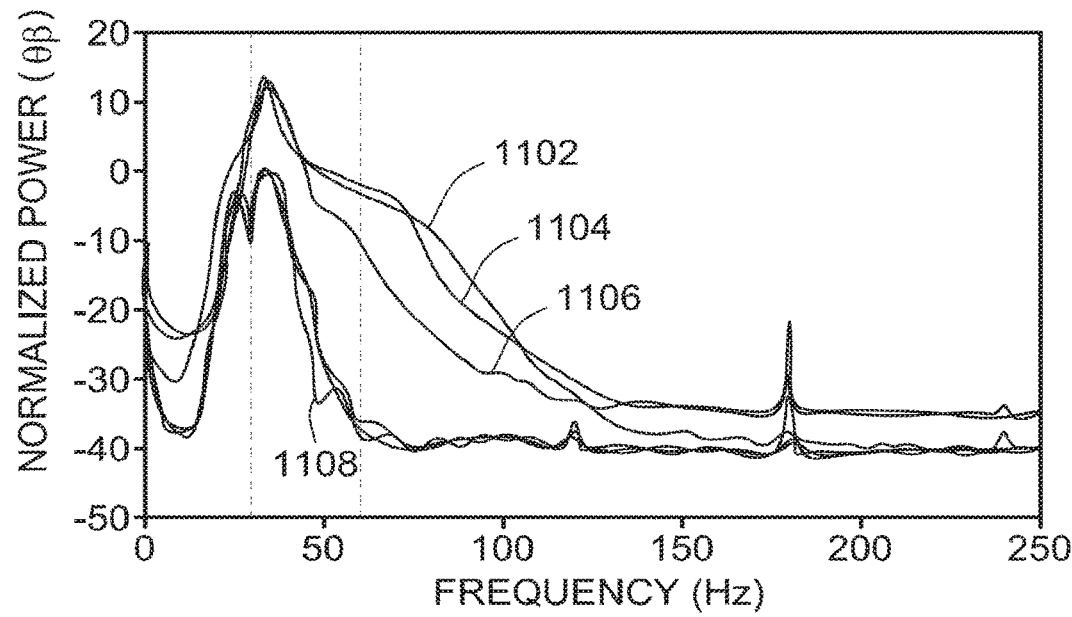
FIG. 11 illustrates a comparison of a single-bodied mattress to the isolation mattress of FIG. 9.

FIG. 11 shows results from the test of the single-bodied mattress compared to the isolation mattress with active and passive regions. Specifically, the results show the PSD and isolation characteristic of the mattress at therapeutic settings (30 Hz-60 Hz), with five measurements at each setting. The isolation mattress was the same as described in FIG. 9. Line 1102 represents readings from the tested single-bodied mattress at the center of stimulation for 1.5 turns. Line 1104 represents readings from the single-bodied mattress measured at the location of an infant's head for 1.5 turns. Line 1106 represents readings from the isolation mattress measured at the active region center 1302a at 2.75 turns of the signal generator, which was determined to produce the same therapeutic amplitude as the single-bodied mattress at 1.5 turns. Line 1108 represents readings from the isolation mattress measured at the passive region center 1304a at 2.75 turns. The output power spectral density of the isolation mattress closely matched the single-bodied mattress from 4 Hz-43 Hz, but the delivered power drops off from 44 Hz-60 Hz. The difference above 44 Hz may have been caused by the outer vinyl skin of the tested isolation mattress internally adhering to the body of the mattress. A similar attenuation was seen in previous single-bodied mattress characterization when a 1.5 kg mass was placed on the mattress.

Figure 12:
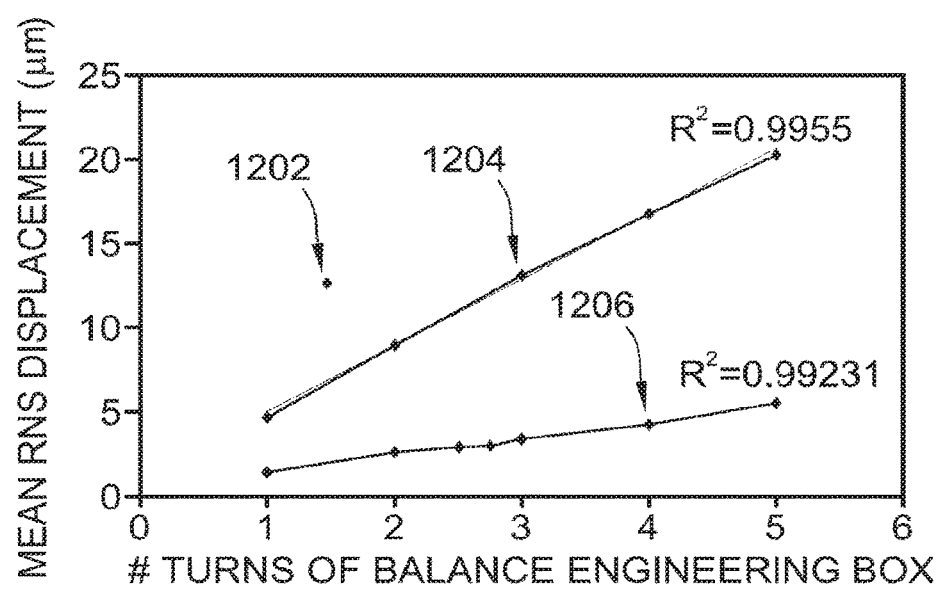
FIG. 12 illustrates a graph of mattress output for the isolation mattress of FIG. 9, comparing the output of active and passive regions.

Referring now to FIG. 12, a graph of mattress output is shown. The graph shows the mattress output versus the signal generator setting (average of 5×100 second measurements). Point 1202 is the output of the single-bodied mattress. Line 1204 is the output of isolation mattress at the active region center 1302a. Line 1206 is the output of the isolation mattress at the passive region center 1304a. Table 1 lists the measured values shown in the graph with a calculation of the percent attenuation between the active region center 1302a and the passive region center 1304a.

TABLE 1

RMS Displacement Values and Percent Attenuation for the Isolation Mattress

| Stimulus Generator setting [turns] | Mean Active Region Center RMS Displacement [μm] | Mean Passive Region Center RMS Displacement [μm] | Active Center to Passive Center Attenuation [%] |
|---|---|---|---|
| 1 | 4.5 | 1.3 | 72.0 |
| 2 | 8.9 | 2.5 | 72.4 |
| 2.5 | 11.0 | 2.8 | 74.7 |
| 2.75 | 12.1 | 2.9 | 76.0 |
| 3 | 13.2 | 3.4 | 74.5 |
| 4 | 16.7 | 4.2 | 74.7 |
| 5 | 20.1 | 5.5 | 72.9 |

As shown in table 1, there was a drastic reduction in displacement between the active center and the passive center. The attenuation between the centers was consistently between 72% and 76% across the tested range. That is, the isolation mattress 900 prevented approximately three quarters of the stimulation of the active region from reaching the passive region.

The secondary positions 1304c, 1306 provide data related to the attenuation of vibration between the approximate the head and body positions of an infant placed on the isolation mattress. Table 2 compares attenuation between an infant's head and body using the above described single-bodied mattress and the isolation mattress 900.

TABLE 2

Comparison of Single-bodied and Isolation Mattresses

| | Stimulus Generator Setting [turns] | Mean Mattress Center RMS Displacement [μm] | Mean Head RMS Displacement [μm] | Attenuation [%] |
|---|---|---|---|---|
| Single-bodied | 1.5 | 12.5 | 11.0 | 12.2 |
| Isolation | 2.75 | 8.4 | 2.6 | 69.5 |

Comparing the attenuation of the overall mattress center to the approximate head location for both mattresses resulted in the isolation mattress showing an improvement of 5.7 times over the single-bodied mattress.

The therapeutic level of stimulation of the single-bodied mattress was determined to be 1.5 turns of the amplifier on the noise generator as determined by comparison to previous tests. Therapeutic level of stimulation may be any stimulation that is capable of altering a sleep state or physiological function of sufficient amplitude to cause harm or pain. This includes subthreshold, subarousal, and/or suprathreshold stimulation. The isolation mattress was tested to determine the turns needed to achieve an equivalent level of output stimulation. It was determined that 2.75 turns was the appropriate therapeutic setting for the isolation mattress. At this setting, the mean root-mean-squared displacement of the center 1302a of the active region 902 is comparable to the therapeutic displacement of the geometric center of the single-bodied mattress.

Sensors for direct monitoring and/or control of mattress surface displacement may be incorporated with the isolation mattress 900. These sensors can include, for example, embedded accelerometers or other vibratory sensors (e.g., pressure sensors, load cells, optical sensors). Such sensors can be used, for example, in modifying the drive signal for the active region in response to weight, loading, or the location of the infant on the mattress. Such sensors can be used, for example, in alerting caregivers to malfunctions or even active cancellation of stimulation in the passive region.

While some of the embodiments of the invention can include a mattress having an active and a passive or isolated region, the invention can be incorporated into other devices such as a mattress pad, a baby carrier and a car seat. In a mattress pad, the isolation region can include vibration and sound absorbing or dampening materials that limit or prevent the stimulation (e.g., vibration or sound) from reaching the isolation region. Baby carriers and car seats can configured to either isolate the stimulation generating element from the remainder of the carrier or car seat or include an isolation region in the area where the infant's head is likely to rest.

Based on growing evidence that subsensory/sub-threshold, stochastic perturbations can impinge upon nonlinear neural control systems and transform unstable states into stability of rhythm. It is, therefore, contemplated that alternative embodiments according to the present concepts may apply subsensory/sub-threshold stochastic stimulation. The subsensory/sub-threshold nature of such stimulation may be effective, as infants, such as those suffering from NAS or colic, are particularly sensitive to sensory stimuli (e.g., sound, light, touch). In accordance with some embodiments, the level of the stimulation can be subsensory/sub-threshold, for example, based on prior exposure, setting the level just below the point at which the infant begins to show signs responding to the stimulation.

In accordance with some embodiments of the invention, the amplitude, frequency and/or period of stimulation can change within a range that produces subsensory/sub-threshold stimulation (e.g., the signal is insufficient to cause sensory cells of the infant to activate and begin signaling) and/or supra-threshold stimulation (e.g., the signals are sufficient to cause sensory cells of the infant to activate and begin firing). In accordance with some embodiments, the stimulation can include periods of both subsensory/sub-threshold stimulation and supra-threshold stimulation according to a predefined or random pattern. In accordance with some embodiments, the stimulation can include periods of only subsensory/sub-threshold stimulation, including periods where the level varies within a predefined range. In accordance with some embodiments, the stimulation can include periods of only supra-threshold stimulation, including periods where the level varies within a predefined range.

Although the present concepts may be described herein with reference to infants suffering from NAS or colic, it is also understood that the embodiments may reduce irritability in infants, regardless of the cause and even though they may not meet the formal criteria for colic.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method for reducing irritability in an infant, the method comprising:
    determining, via one or more sensors, one or more physiological measurements from an infant, the one or more physiological measurements relating to a state of irritability in the infant and including an increase relative to baseline information in one or more of infant movement, infant heart rate, infant temperature, or infant crying;
    determining, via a controller communicatively coupled to the one or more sensors, the state of irritability based on the one or more physiological measurements;
    applying, via an actuator, a stochastic stimulation to the infant based on the state of irritability; and
    based on the stochastic stimulation, reducing the increase in one or more of the infant movement, infant heart rate, infant temperature, or infant crying.

2. The method of claim 1, wherein the infant suffers from Neonatal Abstinence Syndrome (NAS) and the one or more physiological measurements indicate symptoms of NAS relating to the state of irritability.

3. The method of claim 1, wherein the infant suffers from colic and the one or more physiological measurements indicate symptoms of colic relating to the state of irritability.

4. The method of claim 1, wherein the one or more physiological measurements indicate crying lasting for more than three hours, and the stochastic stimulation is applied in response to crying that lasts for more than three hours.

5. The method of claim 1, wherein the actuator is included in a mattress.

6. The method of claim 5, wherein the mattress includes an active region and a passive region, and the stochastic stimulation is only applied via the active region.

7. The method of claim 1, wherein the stochastic stimulation is vibro-tactile.

8. The method of claim 1, where the stochastic stimulation is subsensory.

* * * * *